US009964482B2

(12) United States Patent
Sun et al.

(10) Patent No.: US 9,964,482 B2
(45) Date of Patent: May 8, 2018

(54) DETECTING CLOUDS USING POLARIZED SUNLIGHT

(71) Applicant: U.S. Army Research Laboratory ATTN: RDRL-LOC-I, Adelphi, MD (US)

(72) Inventors: Wenbo Sun, Yorktown, VA (US); Gorden Videen, Silver Spring, MD (US); Michael I. Mishchenko, New York, NY (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 37 days.

(21) Appl. No.: 15/006,752

(22) Filed: Jan. 26, 2016

(65) Prior Publication Data

US 2016/0216198 A1     Jul. 28, 2016

Related U.S. Application Data

(60) Provisional application No. 62/107,662, filed on Jan. 26, 2015.

(51) Int. Cl.
*G01N 21/21* (2006.01)
*G01W 1/02* (2006.01)
*G01N 21/53* (2006.01)
*G01N 21/47* (2006.01)

(52) U.S. Cl.
CPC ........... *G01N 21/21* (2013.01); *G01N 21/538* (2013.01); *G01W 1/02* (2013.01); *G01N 2021/4792* (2013.01); *G01N 2201/0616* (2013.01)

(58) Field of Classification Search
None
See application file for complete search history.

(56) References Cited

U.S. PATENT DOCUMENTS

| 3,721,500 | A | * | 3/1973 | Fugitt | G01N 21/21 250/225 |
| 3,788,742 | A | * | 1/1974 | Garbuny | G01N 21/39 356/218 |
| 4,362,387 | A | * | 12/1982 | Clark | G01J 4/00 356/338 |
| 5,557,040 | A | * | 9/1996 | Inenaga | G01W 1/14 250/559.09 |
| 6,239,873 | B1 | * | 5/2001 | Videen | G01N 21/21 356/369 |

(Continued)

OTHER PUBLICATIONS

W. Sun, G. Videen, and M.I. Mishchenko, "Detecting superthin clouds with polarized sunlight." Geophys. Res. Lett., 41, No. 2, 688-693 (2014).

(Continued)

*Primary Examiner* — Kara E Geisel
*Assistant Examiner* — Jarreas C Underwood
(74) *Attorney, Agent, or Firm* — Eric Brett Compton

(57) ABSTRACT

A novel methodology for detecting cloud particles is disclosed herein. This methodology exploits the optical glory phenomenon. According to one embodiment, a method for detecting clouds includes receiving data from a sensor which is configured to measure polarization of scattered light in a direction substantially opposite to the direction of incident light, and identifying, from the received sensor data, a cloud based on the polarization of the scattered light.

20 Claims, 7 Drawing Sheets

(56) References Cited

U.S. PATENT DOCUMENTS

| | | | | |
|---|---|---|---|---|
| 6,353,392 | B1* | 3/2002 | Schofield | B60H 1/00785 |
| | | | | 318/444 |
| 6,489,915 | B1* | 12/2002 | Lines | G01N 22/00 |
| | | | | 342/26 B |
| 6,680,696 | B1* | 1/2004 | Hayashi | G01S 5/0027 |
| | | | | 342/357.2 |
| 7,440,102 | B1* | 10/2008 | Videen | G01N 21/49 |
| | | | | 356/342 |
| 7,532,325 | B2* | 5/2009 | Ahmed | G01J 3/02 |
| | | | | 356/317 |
| 7,823,836 | B2* | 11/2010 | Ho | B64G 1/1021 |
| | | | | 244/158.6 |
| 7,986,408 | B2* | 7/2011 | Ray | B64D 15/20 |
| | | | | 356/342 |
| 8,144,325 | B2* | 3/2012 | Ray | B64D 15/20 |
| | | | | 356/342 |
| 9,041,926 | B2* | 5/2015 | Ray | G01S 17/95 |
| | | | | 356/342 |
| 2001/0048078 | A1* | 12/2001 | Stair | G01N 21/21 |
| | | | | 250/340 |
| 2008/0007451 | A1* | 1/2008 | De Maagt | G01S 13/89 |
| | | | | 342/351 |
| 2011/0222063 | A1* | 9/2011 | Izawa | G01N 21/3504 |
| | | | | 356/437 |

OTHER PUBLICATIONS

W. Sun, R. R. Baize, G. Videen, Y. Hu, and Q. Fu, "A method to retrieve super-thin cloud optical depth over ocean background with polarized sunlight," Atmos. Chem. Phys., 15, 1-10, 2015.

C.F. Bohren and D.R. Huffman, "Absorption and Scattering of Light by Small Particles." Wiley, New York 1983, p. 52.

* cited by examiner

DETECTING CLOUDS USING POLARIZED SUNLIGHT

CROSS REFERENCE TO RELATED APPLICATION(S)

This application claims the benefit of U.S. Provisional Patent Application No. 62/107,662 filed Jan. 26, 2015, the disclosure of which is herein incorporated by reference in its entirety for all purposes.

GOVERNMENT INTEREST

The invention described herein may be manufactured, used and licensed by or for the U.S. Government without the payment of royalties thereon. Research underlying this invention was funded, in part, under NASA Glory fund 09-GLORY09-0027.

BACKGROUND OF THE INVENTION

Field

Embodiments of the present invention generally relate to meteorology and weather detection, and more specifically, to detecting clouds using polarized sunlight.

Description of Related Art

Super-thin cirrus clouds with optical depths smaller than approximately 0.3 exist globally. These clouds are important to the radiation energy balance of the Earth. They also can affect the remote sensing of aerosols, surface temperature, and atmospheric gases. For example, the aerosol optical depth (AOD) from NASA's Moderate Resolution Imaging Spectroradiometer (MODIS) data could be overestimated by about 100% when these clouds exist. Failing to detect these clouds, the sea surface temperature (SST) retrieved from NASA's Atmospheric Infrared Sounder (AIRS) satellite data is about 5K lower at tropical and mid-latitude regions, where occurrence frequency of these clouds is high. Climate models must incorporate these clouds correctly in order to account for the Earth's radiation energy budget. To inter-calibrate other satellite sensors with NASA's future Climate Absolute Radiance and Refractivity Observatory (CLARREO) measurements, knowledge of these clouds is necessary for correcting these sensors' measurement errors due to light's polarization.

Due to uncertainties in surface reflectance, transparent super-thin clouds generally cannot be detected by satellite imagers, like the MODIS and the Advanced Very High Resolution Radiometer that only measure the total radiance of the reflected solar light. The resulting data products of many satellite and ground measurements are biased by these undetected clouds. Using a strong water vapor absorption channel such as the 1.38 μm radiance to exclude the surface and low-layer effects can be effective on high cirrus, but may encounter difficulties for atmospheres with low water vapor. The reliability of this method is also questionable if the clouds' optical depth is smaller than about 0.5, when their backscattered intensity is low. In addition, super-thin clouds may also exist in the lower layers of the atmosphere where there is ample water vapor. The sensitivity of the 1.38 μm channel is weak in this region, hampering detection capabilities.

NOAA's polar orbiting High Resolution Infrared Radiation Sounder multispectral infrared data are usually used with the $CO_2$-slicing method for detecting thin cirrus clouds. However, for super-thin clouds, this requires the radiance of their background atmosphere and surface to be very close to that of the reference clear sky environment, which can be difficult as the terrestrial background changes on spatial and temporal scales. In addition, this method is problematic when the difference between clear-sky and cloudy radiance for a spectral band is less than the instrument noise, as for super-thin clouds.

Currently, NASA's Cloud-Aerosol Lidar and Infrared Pathfinder Satellite Observation (CALIPSO) satellite is the only instrument in orbit that can detect super-thin clouds. The lidar fires a laser through the atmosphere and detects the signal returning. The time and strength of the returning signal is analyzed to determine where in the atmosphere particles are located and how many there are. While this instrument is effective, it is extremely expensive to operate and can only measure a small region (i.e., due to the narrow thickness of the laser beam).

Improvements in cloud detection would be useful, as they would improve weather predictions and calculations of the energy budget.

SUMMARY OF THE INVENTION

A novel methodology for using passive polarimetric data to detect cloud particles is disclosed herein. This methodology exploits the optical glory phenomenon. According to an embodiment, a method for detecting clouds includes: receiving data from a sensor which is configured to measure polarization of scattered light in a direction substantially opposite to the direction of incident light; and identifying, from the received sensor data, a cloud based on the polarization of the scattered light. At least one processor may be used for executing the method embodiments, for example.

In the method, the sensor may be configured to measure scattered light over a range of about 0-20° from the exact backscattered light direction, and more particularly, the sensor may be configured to measure especially the scattered light over a range of about 5-10° from the exact backscattered light direction as this is the location in the glory where it is believed that the polarization signal is the greatest.

In some embodiments, the sensor is configured to detect the s-polarization and p-polarization intensities of the measured scattered light. In this way, a cloud is identified if the detected p-polarization measurement is greater than the s-polarization measurement of the scattered light direction.

In further embodiments, the sensor and/or image processor associated therewith may be configured to directly provide the Stokes Parameters Q, U and I of polarization. Thus, in some implementations, the method further calculates the degree of polarization normalized Mueller matrix element P12/P11 from the Stokes Parameters of polarization as follows:

$$P12/P11 = (I_S - I_P)/(I_S + I_P),$$

where $I_S$ is the intensity of the s-polarized component of the light and $I_P$ is the intensity of the p-polarized component of the light. In this manner, a cloud is identified if the calculated P12/P11 is negative near the backscattered light direction. And, in other implementations, the method further calculates the angle of linear polarization (AOLP) from Stokes Parameters of polarization as follows:

$$AOLP = \frac{1}{2}\tan^{-1}\left(\frac{U}{Q}\right) + \alpha_0,$$

where $\alpha_0=0°$ if Q>0 and U≥0; $\alpha_0=180°$ if Q>0 and U<0; and $\alpha_0=90°$ if Q≤0. In this manner, a cloud is identified if the calculated AOLP≤about 60° or ≥about 120°.

The measurement wavelength may be judiciously chosen for improved measurements. For instance, in some implementations, the sensor data may be measured at a wavelength of about 1.38 μm. The 1.38 μm wavelength is the location of a water-absorption band that may enhance the signal. It has been used in other applications, so it is likely that it may increase sensitivity. In other implementations, the sensor data is measured at a wavelength of about 670 nm. By using this longer solar wavelength, the contribution of molecular scattering can be reduced leading to more effective measurements.

According to an embodiment, the sensor can be located on a satellite orbiting the Earth. Sensor data from the satellite can be transmitted to a ground station, and/or the transmitted sensor data can be received at the ground station.

Unlike lidar, which uses a laser light source, passive system embodiments can use natural light from the sun. Thus, only scattered sunlight will be measured by the sensor in this way. Such systems are much less expensive to operate and are especially desirable for satellite systems.

The method can further identify, from the received sensor data, a super-thin cloud based on the polarization of the scattered light. Super-thin clouds are a type of cloud, which cannot be seen easily visually.

According to a further embodiment, a method for detecting cloud particle includes: receiving data from a sensor which is configured to measure polarization of an optical glory associated with a cloud; and identifying, from the received sensor data, cloud particles based on the polarization of the optical glory.

And according to yet another embodiment, a system for detecting clouds includes: a sensor configured to measure polarization of scattered light in a direction substantially opposite to the direction of incident light; and a processor configured to identify, from the measured sensor data, a cloud based on the polarization of the scattered light. In the system, the sensor can include at least one polarizer which filters incoming light having p-polarization, a lens which focuses the filtered light, and an image detector which receives the focused light. The polarizer(s) can include (i) a rotating polarizer or (ii) multiple polarizers which are offset in angular orientation.

These and other embodiments are discussed in more detail below.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. The drawings are not to scale unless so stated. It is to be noted, however, that the appended drawings illustrate only typical embodiments of this invention and are therefore not to be considered limiting of its scope, for the invention may admit to other equally effective embodiments. These embodiments are intended to be included within the following description and protected by the accompanying claims.

DETAILED DESCRIPTION

Figure 1:
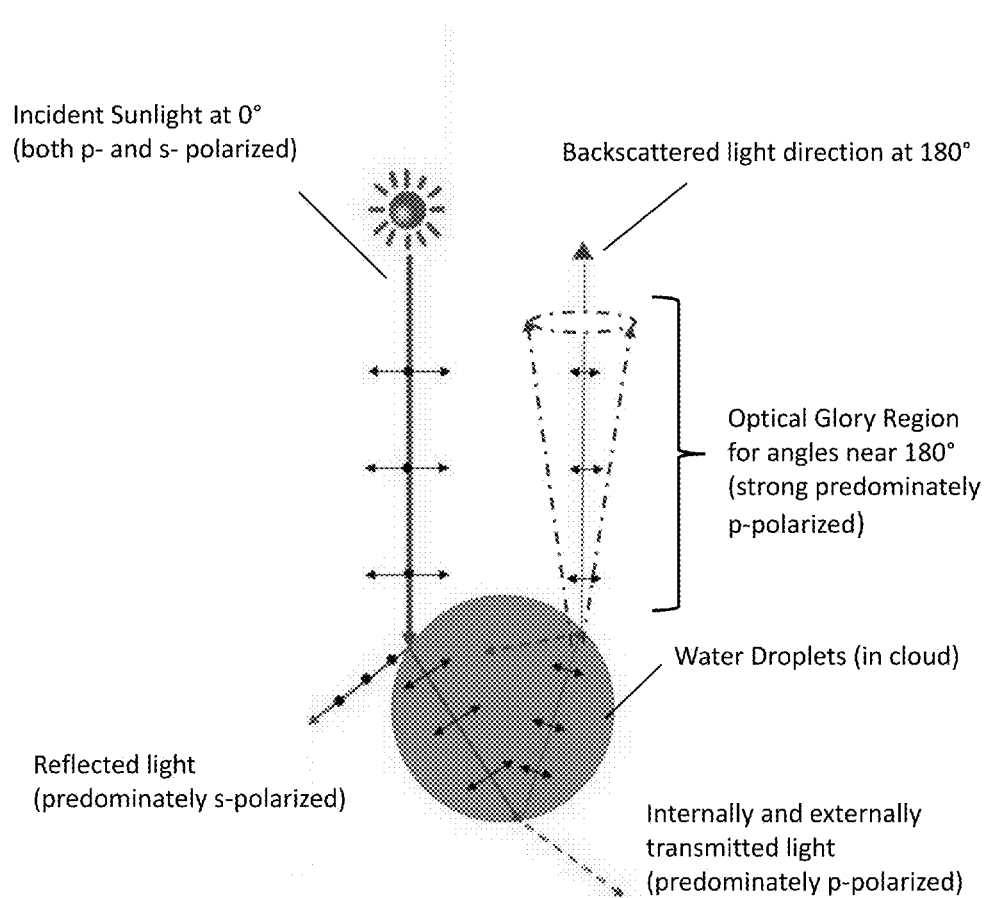
FIG. 1 shows the optical glory mechanism which produces the polarization that is detected according to embodiments of the present invention.

The inventors studied solar radiation backscattered from clouds with both satellite data and a radiative-transfer model. They have found that, while the dominant backscattered electric field from the clear-sky Earth-atmosphere system is nearly parallel to the Earth surface, when clouds are present, this electric field can rotate from the parallel to the perpendicular direction. And, more particularly, they identified that a distinct feature, i.e., characteristic of clouds, is responsible for this polarization change. This feature is the result of the optical phenomenon known as a glory. Results of this discovery and initial findings are reported in more detail in the article by W. Sun, G. Videen, and M. I. Mishchenko, titled "Detecting super-thin clouds with polarized sunlight." *Geophys. Res. Lett.*, 41, no. 2, 688-693 (2014), which was incorporated in and formed a basis of the aforementioned '662 provisional application. The inventors used data obtained from the PARASOL satellite to verify the novel methodology.

The methodology uses a detected polarization signal that has been measured from light that has been scattered to locate the presence of clouds. Such clouds may be located in the atmosphere, or they may be located in fluids (like bubbles, contaminants, and micro-organisms). The term "cloud" as used herein means a mass of condensed water vapor and/or particles present or floating in the medium. That medium may be the Earth's atmosphere, typically high above the ground; this may include typical weather clouds, for instance. Such clouds are usually classified by their shapes and locations. They have a significant effect on the weather (and climate) affecting ground temperatures. In addition, the clouds may be present in other media such as fluids (like bubbles, contaminants, and micro-organisms, etc.).

Super-thin clouds are a type of cloud. While there is no specific definition in the art, "super-thin clouds" are typically clouds that cannot be seen easily visually; however, they can have a significant effect on the radiation budget by scattering light back into space. A rough rule-of-thumb is that they are particles in the atmosphere, usually composed of liquid water or ice and their optical thickness is less than 0.3. Optical Thickness is a term well-known in the art that refers to the natural logarithm of the ratio of incident to transmitted radiant power through a medium. In this case, the medium is the atmosphere containing the cloud. Unfortunately, because super-thin clouds cannot readily be seen, they are not easily classified. The major exception is cirrus clouds which are thin wispy clouds in the upper atmosphere. Cirrus are a prime concern as they have a significant impact on the radiation budget (which is important for radiation-budget considerations), in addition to covering a significant portion of the Earth. Thin cirrus clouds are generally a mixture of various ice crystal shapes such as hexagonal columns, plates, droxtals, bullet rosettes, and aggregates. There also can be, for instance, thin fog, in the lower atmosphere. Initial model results demonstrate that the methodology is effective for detecting super-thin cirrus clouds. Such clouds are too thin to be sensed using any current passive satellite instruments. Using the innovative methodology, the inventors have identified the presence of such clouds in regions that would be likely identified as "clear sky," with conventional means.

The methods and systems described below can be used to detect super-thin clouds by measuring the polarization of scattered light present in the optical glory region. The optical glory is typically located within a region of smaller angular deviation from the exact backscattered direction, which is opposite to the direction the incident light travels. By judiciously positioning a polarimeter, the linear polarization state of scattered light, determined from the intensities of the components of light polarized both parallel and perpendicular to the scattering plane can be detected and measured. The polarimeter thus should be arranged to measure the linear polarization state of light in the backscattered direction and to detect this polarization. If the polarization state is determined to be predominantly within the scattering plane, it is an indication that cloud particles are present.

The novel methodology is a radically different approach to monitor atmospheric particles. It may be passive (i.e., using the sun as a source), and it uses the scattered light polarization state in the backscattering direction. Aside from the polarization measurement, the other critical aspect of this step is the precise viewing region under consideration. Unlike other conventional monitoring systems, the methodology exploits the optical glory phenomenon which typical occurs in specific regions centered about the exact backscattered direction. The inventors have tested this methodology using polarization measurements obtained from the PARASOL satellite.

FIG. 1 illustrates the optical glory phenomenon which the present invention exploits to detect the presence of clouds. The optical glory is caused by sunlight interacting with the tiny water droplets in clouds. For ease of explanation, only a single water droplet is illustrated; although, in actuality, there are many droplets present in a cloud. Incident sunlight strikes the water droplet. At the surface of the droplet, some light is reflected and some light it transmitted inside. The incident sunlight includes radiation/light which is both p-polarized and s-polarized. The terms "radiation" and "light" as used herein include electromagnetic radiation in the ultraviolet, visual, and/or infrared spectra.

Natural solar radiation can be polarized by surface reflections as well as by scattering from atmospheric molecules and particles. (In this figure, p-polarization is identified with arrows, ↔, and s-polarization is identified with a dot, •. The ↔ indicates the direction of the electric field vector of this component is within the page; whereas, the • indicates the direction of the electric field vector of this component is perpendicular to the page). When sunlight propagates through the clear atmosphere and is scattered back toward the Sun, the resulting signal is nearly unpolarized when the solar zenith angle (SZA) is not larger than about 40°. The residual polarization in this direction is caused by asymmetries in the system, for instance, due to preferentially oriented ocean waves or nonzero angles between incidence and observation. By considering a longer solar wavelength, such as 670 nm, the contribution of molecular scattering can be reduced.

In this illustration, the sun is shown at optical noon, i.e., directly overhead. The actual angle of incident sunlight will vary at other times of the day; however, the angle of the incident sunlight may be relatively defined as 0°. Reflected light from an interface is predominantly of s-polarization; whereas, transmitted light is predominantly of p-polarization. This is a consequence of the Fresnel equations, which can be used to characterize the amount of light of each polarization state is reflected by and transmitted into a planar interface.

The optical glory is an angular region of high light intensity which typically consists of one or more concentric, successively dimmer rings of light. The glory prominence is dependent on particle morphology and absorption. Spherical droplets in water clouds can produce an especially strong glory. The glory generally extends over a small range of angles from the exact backscatter direction, typically between 0 and ±20° and is accompanied by a very strong p-polarization component. The predominant p-polarization of the glory is believed to be due to the internally transmitted light within the droplet which is emitted in the opposite direction to the incident sunlight direction due to resonance effect. Assuming the incident sunlight direction is 0°, the backscatter direction is 180°. The intensity of the glory is greatest in the exact backscattering direction; however, at this location, the light is typically unpolarized. As we move from the backscatter location, the intensity decreases, while the polarization favors the p-polarization state. The surge in intensity typically extends some 10-20°, which is approximately the extent of the scattered light favoring the p-polarization state, with the maximum amplitude of p-polarization state occurring at approximately halfway within this range, approximately 5-10°. This would be where the signal is greatest. The angular extent of the glory depends strongly on the size of the particles in the cloud. The larger the particles, the smaller is the angular extent. Cloud particles tend to range from approximately 1 to 100 μm in size.

Model results demonstrate that this very strong p-polarization feature can be used to detect super-thin clouds. For instance, these results demonstrates that sub-visual water clouds having an optical depth (OD) of only 0.01 still display a prominent polarization feature. More, these results have been shown to be especially successful, particularly, in detecting and identifying cirrus clouds having an optical depth of only about 0.06 and super-thin liquid water clouds having an optical depth of only about 0.01. Such clouds are too thin to be sensed using any current passive satellite instruments. Thus, according to embodiments of the present invention, by imaging and determination of the linear polarization of solar radiation associated with the optical glory that is backscattered, clouds, super-thin clouds, and other phenomena may be detected and identified.

Figure 2:
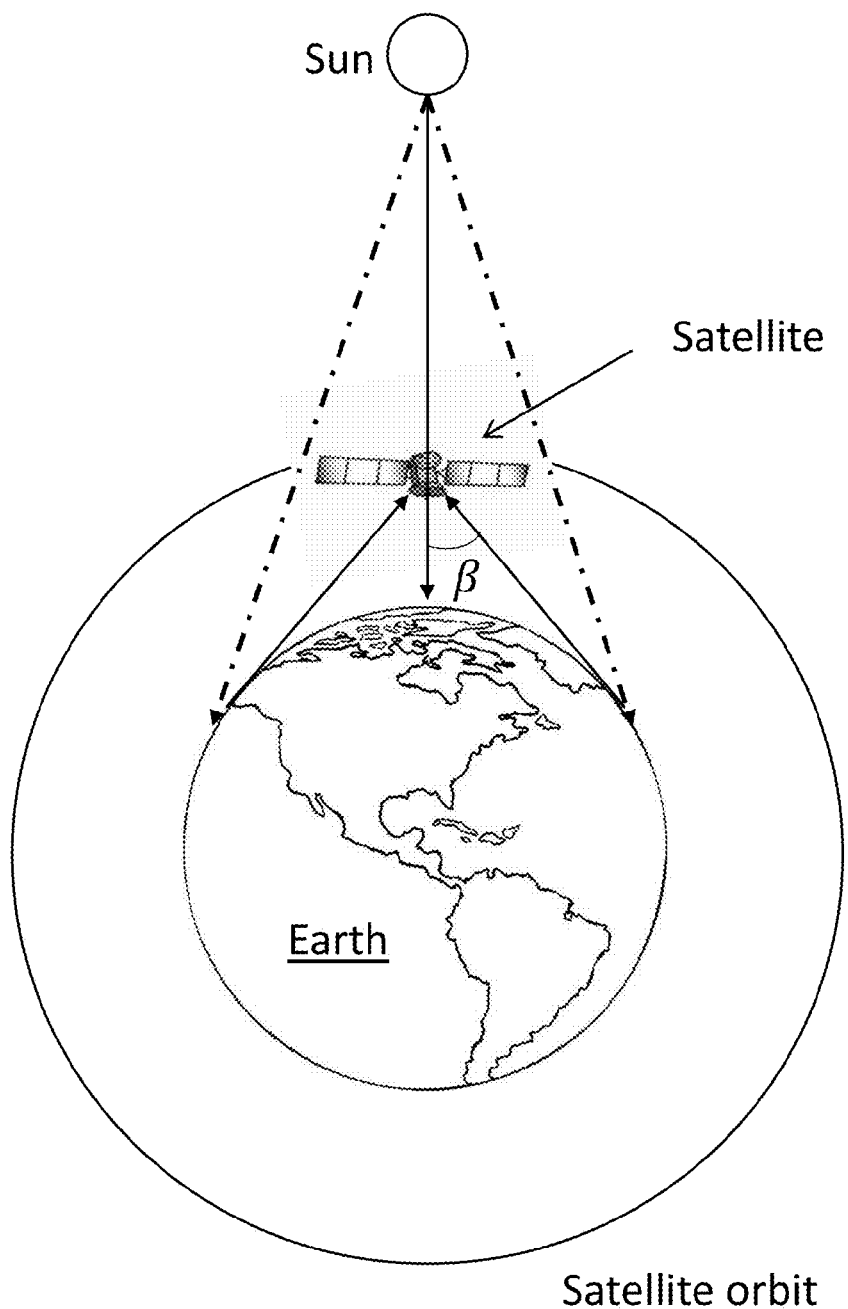
FIG. 2 shows a schematic of the orientation or a satellite to visualize the optical glory according to an embodiment of the present invention.

FIG. 2 shows a satellite system which may be used for imaging of the atmosphere, in some embodiments, in practicing the present invention. Sensor instrumentation for detection of the optical glory may be located on a satellite in orbit about the Earth, as shown, or perhaps some other planet or celestial body. The instrumentation is equipped to measure the polarization properties of the scattered light in a direction opposite to the incident sunlight direction.

A polar-orbit is shown in this drawing; this particular orbit is made by the CALIPSO satellite. However, any orbit may be used. The key aspect of the satellite's orbit is that it passes between the Sun and the Earth, or at least very near to it. In practice, the satellite should be substantially co-aligned with the Sun and Earth—i.e., such that the phase angle (defined as the angle between rays connecting a point of observation on the Earth and Sun and a ray connecting the point of observation on the Earth and Satellite) is nearly zero. The satellite scans portions of the atmosphere above the Earth. The phase angle β is shown in the diagram. The orientation shown, in which the ray of observation passes through the center of the Earth is optimal because a greater area of the atmosphere may be imaged at one time. Although, the satellite also might be located a little ahead or behind the sun in actuality.

The satellite instrumentation will be positioned to image the atmosphere above the Earth, which will cover the phase angle β. The satellite may be equipped with a polarimeter, i.e., an instrument for measuring the polarization of light, facing the earth in the sunlight direction. This system is passive in that it uses the sun as the light source. (FIGS. 4A and 4B, for instance, show some embodiments of a polarimeter). As such, operational costs are much lower as this device can be put onto a satellite with other devices. Perhaps most importantly (compared to other conventional imaging systems, such as CALIPSO mentioned above) is that with one image, clouds can be identified over a large region of the atmosphere. Also it can be used discretely.

The satellite and instrumentation data may be transmitted from the satellite to a ground station. While satellite-based sensor instrumentation and imaging is disclosed, data might alternatively be captured with high-altitude air-based platform sensors, located on high flying airplanes, weather balloon, drones, etc. The sensor instrumentation might also be terrestrially based (for clouds in solutions or water).

The incident light used by the methodology preferably comes from the sun making it a passive system. But, in other embodiments, it could use light from a laser or from some other light source making it active. The latter setup can be similar to the systems disclosed in U.S. Pat. No. 7,440,102, herein incorporated by reference. A system such as this could be used to measure the polarization, but this probably is not ideal as the polarization is measured only along a line. Instead, it would be more desirable to measure polarization in a plane, i.e., an image. Thus, in an embodiment, a polarization beam-splitter that transmits one polarization state and reflects another could be further used.

Figure 3:
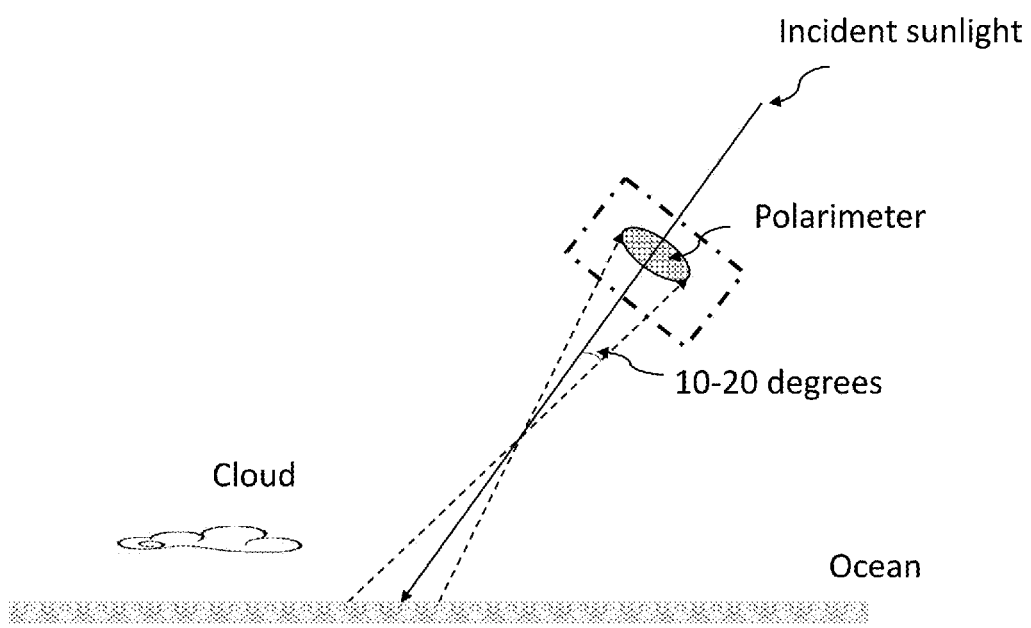
FIG. 3 shows a schematic of a scanning arrangement according to an embodiment of the present invention.

FIG. 3 shows a more detailed example of imaging of the atmosphere in FIG. 2, which happens to be over the ocean. Clouds can be anywhere, although of primary interest are the cirrus clouds located at extremely high altitudes; in these clouds, there are only just a couple or fewer particles per liter. Atmospheric conditions are constantly changing; more or less clouds thus may be present at any given time. In this example, the majority of the sky is clear with only a single cloud mass illustrated.

Figure 4A:
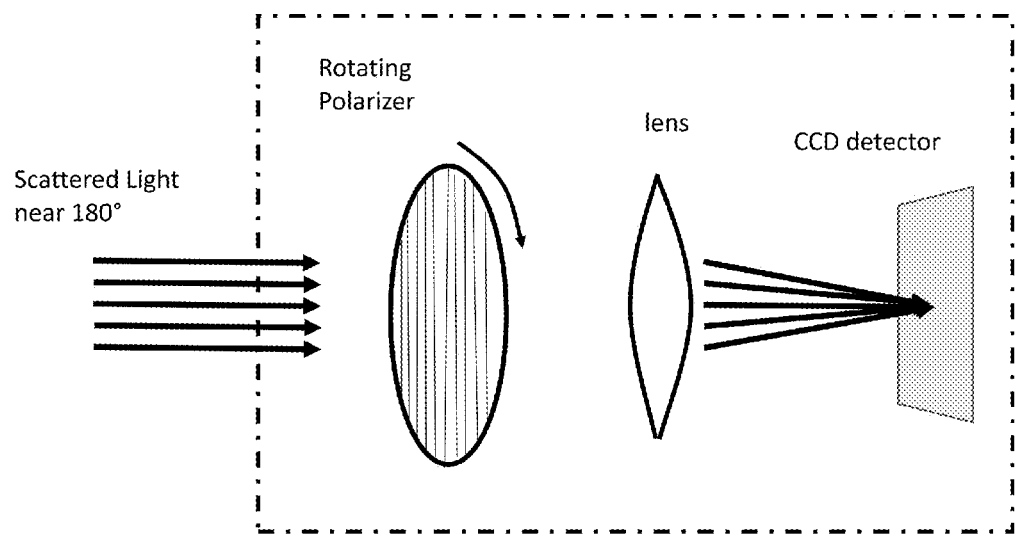
FIGS. 4A and 4B show two schematics of an imaging polarimeter according to embodiments of the present invention.
Figure 4B:
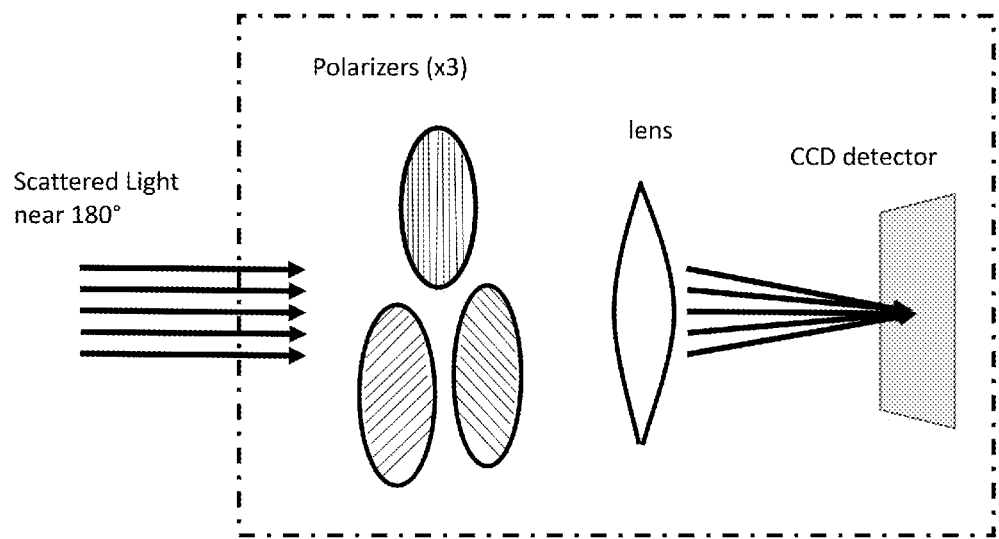

The rectangular box (in dotted line) represents the polarized-imaging instrumentation, embodiments of which are shown in greater detail in FIGS. 4A and 4B. As an example, the instrumentation may include a CCD detector configured to measured polarization of light which is positioned to image a region of the Earth's atmosphere. The field of view of the polarimeter should be of sufficient phase angle β such that the glory can be imaged. The polarization of reflected sunlight can be used to identify clouds as described below.

FIGS. 4A and 4B show two polarimeter instrumentation sensor configurations according to embodiments of the present invention. The instrumentation is equipped to measure the polarization properties of the scattered, for example, by either rotating a linear polarizer or by inserting different linear polarizers within the optical train. This can be done in a variety of ways using common equipment.

The polarimeter instrumentation or sensor may include at least one polarizer, a lens and an image detector. Scattered light is received by the sensor and passes through at least one polarizer, which is an optical filter that passes light of a specific polarization and blocks waves of other polarizations. Here, linear polarization is measured in both the p- and s-polarization states is to be filtered and measured. The lens then focuses the filtered light onto the image sensor. The image sensor may be a two-dimensional or array sensor, such as a charge-coupled device (CCD) detector.

Unlike other monitoring systems, only the angular region covering the region of p-polarization of the optical glory, for example, extending some ±0-20° from the exact backscattered direction in the vertical zenith angle direction is of particular interest.

In the sensor embodiment shown in FIG. 4A, the incident light that has been scattered by the atmosphere passes through a rotating polarizer, and is then focused by a lens onto an image detector. This may be a CCD detector, for instance. The signal is measured multiple times as the polarizer is rotated. The different polarization states may be measured by making one measurement in one polarization state, the p-state for instance, and then making another measurement in the orthogonal polarization state, the s-state for instance. The ideal configuration measures polarization in three polarization states whose electric field components are oriented 60° apart. Using linear combinations of these three measurements, the electric field at any polarization angle may be determined. From these series of measurements, the linear polarization state, including its magnitude and angle of orientation, can be retrieved. In another sensor embodiment, shown in FIG. 4B, three separate polarizers are used that are offset in angular orientation, each one sixty degrees from the other. From measurements with each of these three polarizers in place, the linear polarization can be retrieved. This latter method is employed by the Hubble Space Telescope, for instance.

A key feature of implementation is aligning the instrumentation (by orienting the satellite, for instance), so that the polarization is retrieved from the atmosphere at optical glory angles, of approximately 0-20° from the backscatter direction. The backscatter direction is determined from the position of the sun, the satellite position and the location on the Earth that it is imaging.

Figure 5A:
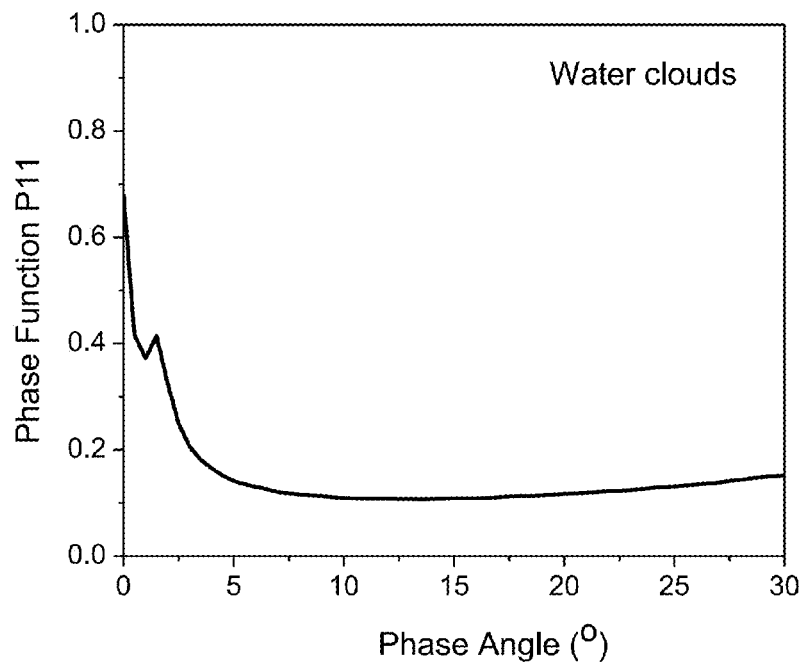
FIGS. 5A and 5B show calculated scattering intensity and polarization, respectively, as a function of phase angle in the backscattering region for water clouds composed of spherical droplets.
Figure 5B:
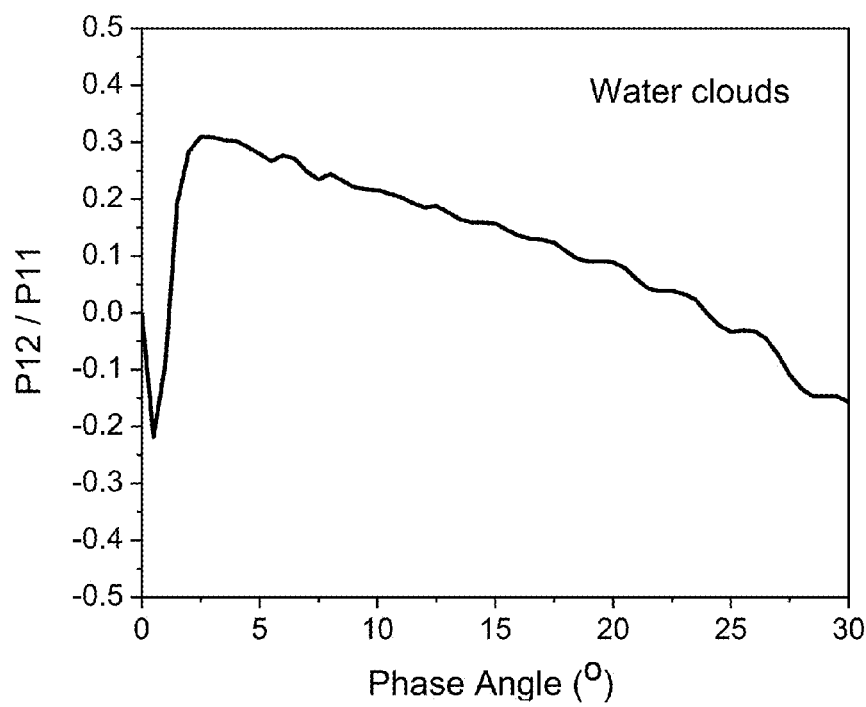

FIGS. 5 and 6 are plots showing exemplary data relating to the optical glory as measured. The plots of FIG. 5 show the total intensity (FIG. 5A) and linear polarization (FIG. 5B) as a function of phase angle from a liquid water cloud. The exact backscattering direction is at 0°. The plots only show the backscattering region, i.e., from about 0-30°, highlighting the optical glory. As apparent, there is a surge in intensity and also a tendency for polarization to acquire negative values near the exact backscattering direction. These negative values are indicative of the p-polarization state; whereas, positive values are indicative of the s-polarization state. In this case, the droplets making up the cloud are large and the glory extends a couple degrees from the exact backscattering direction. For smaller droplets, the extent of the glory is greater.

Figure 6A:
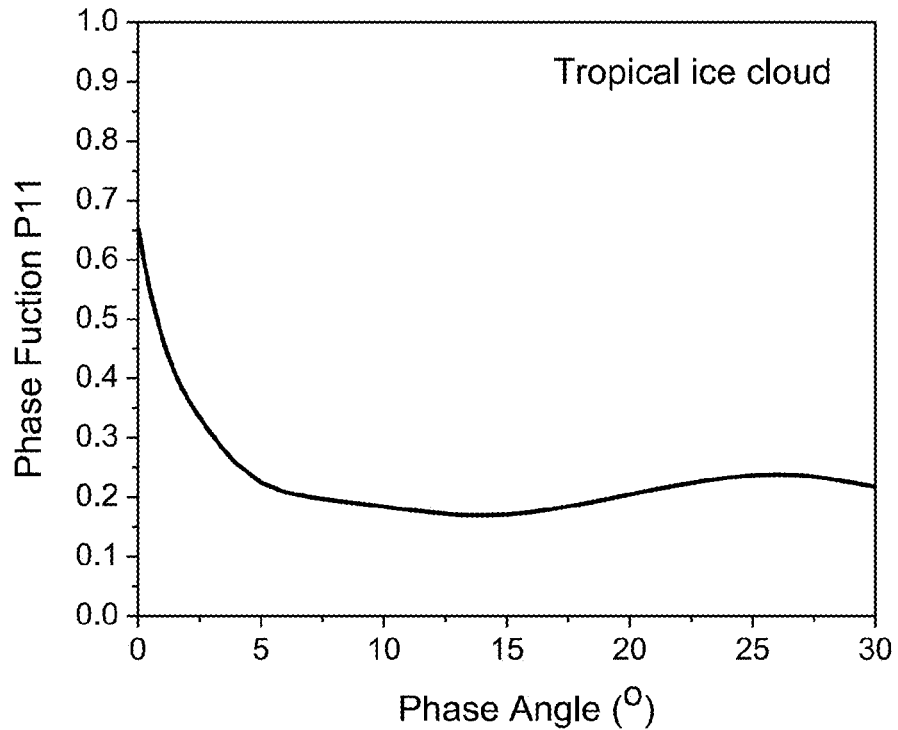
FIGS. 6A and 6B show calculated scattering intensity and polarization, respectively, as a function of phase angle in the backscattering region for tropical ice clouds composed of irregularly shaped particles.
Figure 6B:
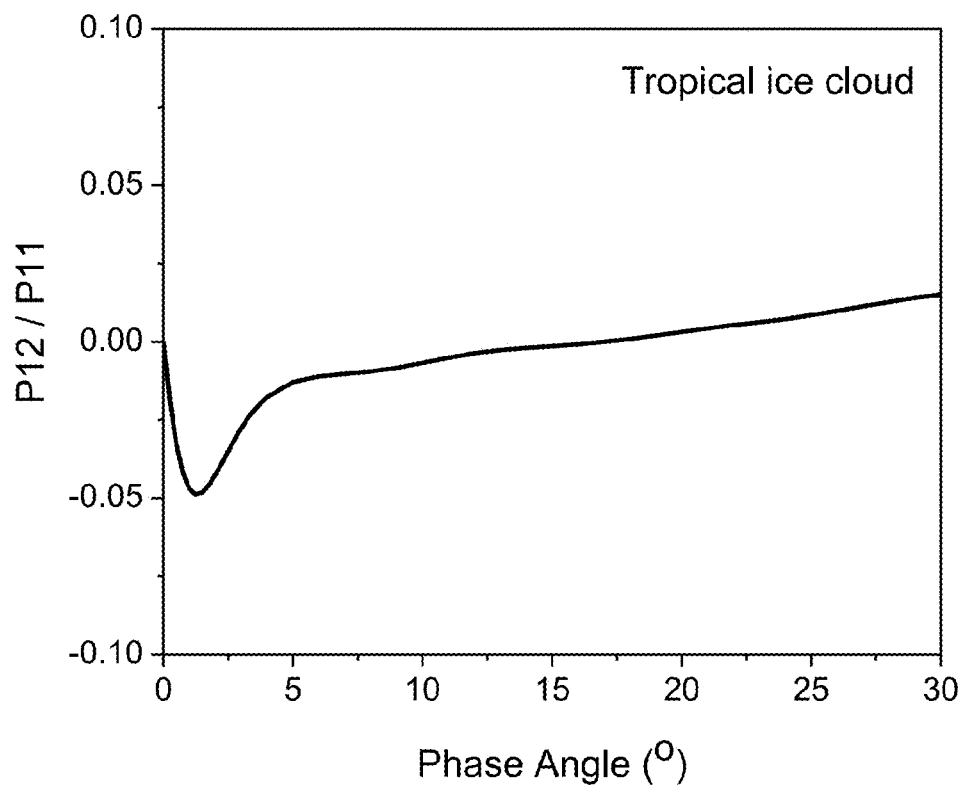

The plots of FIG. 6 show the total intensity (FIG. 6A) and linear polarization (FIG. 6B) of light scattered from a water-ice cloud. The exact backscattering direction is at 0°. The plots only show the backscattering region, i.e., from about 0-30°, highlighting the optical glory. It can be seen that there is surge in intensity and also a drop in the negative polarization to negative values near the backscattering direction. In this case, the particles making up the cloud are large and the glory extends about 8° from the exact backscattering direction. For smaller particles, the extent of the glory is greater. It is noted that the glory is weaker for ice crystals than for droplets and that the negative polarization is weaker than in the plots of FIGS. 5A and 5B.

The measured polarization may be analyzed in many ways. If linear polarization is measured directly by the instrumentation, this data can be used directly. This linear polarization is examined to see if the p-polarization state dominates the signal, i.e., it is greater than the s-polarization, indicative of the optical glory. If it is, then clouds or super-thin clouds are detected and identified. For instance, the detected polarization signal is either positive (indicating s-polarization is dominant) or negative (indicating p-polarization is dominant). If it is negative, then the cloud particles are present in sufficient quantity. The modeling has suggested a lower limit of the Optical Thickness of the cloud that can be detected.

For other polarimeter instrumentation embodiments, Stokes parameters may be used for understanding polarization. The angle of linear polarization (AOLP) is an important characteristic of polarization, which can be defined in terms of Stokes parameters. The Stokes parameters are a set of values that describe the polarization state of electromagnetic radiation well-known in physics. The Stokes parameters I, Q, U, and V can be determined from measurements of the scattered light, where I is the total radiance of light, Q and U describe linearly polarized radiation, and V describes the circularly polarized radiation. The Stokes parameters I, Q, U, and V can be calculated from solar radiance measurements as is known in the art. See, e.g., C. F. Bohren and D. R. Huffman, "Absorption and Scattering of Light by Small Particles," Wiley, New York 1983, page 52 for equations, herein incorporated by reference. Some sensor instrumentations can measure and/or provide the Stokes parameters I, Q, U, and V of the scattered light directly. For instance, the aerosol polarimetry sensor which would have been a part of NASA's Glory satellite, for example, could have provided this data.

Since the circularly polarized component of radiance reflected by the ocean-atmosphere system is negligible (V≈0), the angle of linear polarization (AOLP) can be defined in terms of Stokes parameters according to equation 1 as follows:

$$AOLP = \frac{1}{2}\tan^{-1}\left(\frac{U}{Q}\right) + \alpha_0, \quad (1)$$

where $\alpha_0=0°$ if $Q>0$ and $U\geq 0$; $\alpha_0=180°$ if $Q>0$ and $U<0$; and $\alpha_0=90°$ if $Q\leq 0$.

Because of the variations in surface reflections and atmospheric profiles, using total reflection intensity to detect super-thin clouds is generally difficult from space. Making the total radiance measurements at a wavelength of about 1.38 μm, though, could enhance the detection of super-thin clouds and improve retrieval of aerosol, water vapor or other gases, and surface temperature from satellite data. (The 1.38 μm wavelength is the location of a water-absorption band that may enhance the signal. It has been used in other applications, so it is likely that it may increase sensitivity).

However, unlike total radiance, the AOLP parameter is insensitive to surface roughness and absorption by atmospheric water vapor and other gases, which makes the polarization measurement robust in different environmental conditions, even when the detected components are within the lower layers of the atmosphere. An analogous quantity to the AOLP is the normalized Mueller matrix element P12/P11. This quantity varies between +1 and −1 and is a measure of how strong a scattering system can linearly polarize incident light upon it. If it is positive, it means that the light is s-polarized and if it is negative, it means that the light is p-polarized. While the AOLP and normalized Mueller matrix element P12/P11 are different values, they provide the same information with respect to whether or not the light has a dominant p-polarization component. This information also is contained in the Stokes components Q and U, mentioned above.

The normalized Mueller matrix element P12/P11 can be calculated using the equation 2 as follows:

$$P12/P11 = (I_S - I_P)/(I_S + I_P) \quad (2)$$

where $I_S$ is the intensity of the s-polarized component of the light and $I_P$ is the intensity of the p-polarized component of the light.

In examining P12/P11, one is only concerned with the sign—i.e., whether it is positive or negative. If it is negative, then the light is p-polarization dominant, and thus is indicative of clouds, super-thin clouds, or other particles in the atmosphere. Although super-thin clouds can cause changes in P12/P11 of the reflected light, the dynamic range of this quantity may be insufficient to unambiguously identify super-thin clouds if the background polarized reflection is uncertain.

Figure 7:
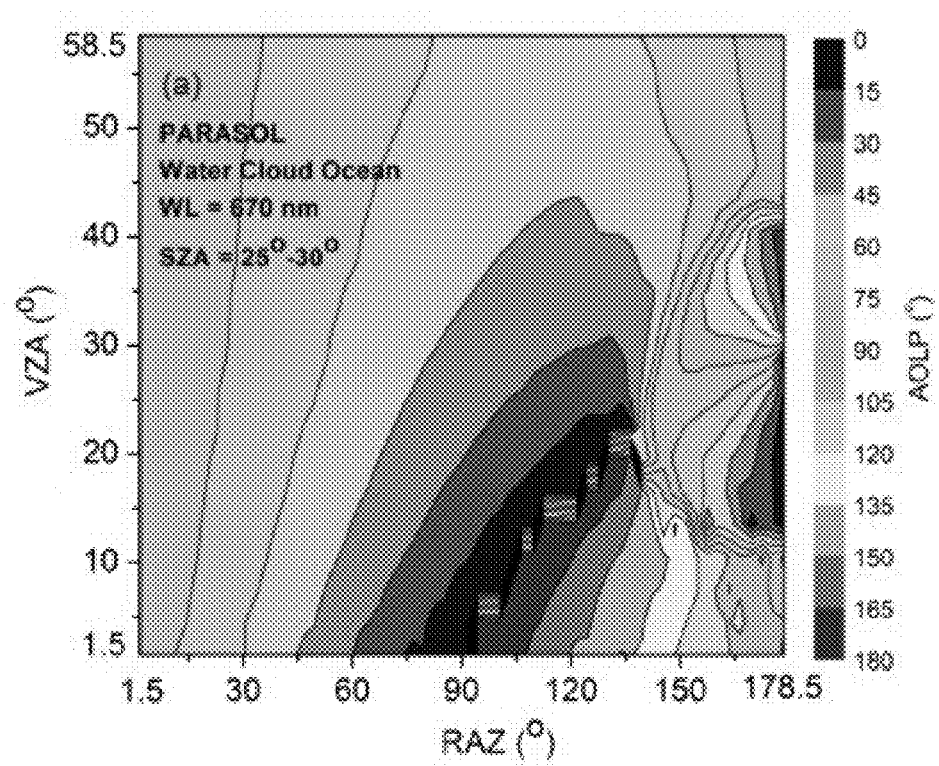
FIG. 7 shows the results of the AOLP measurements from the PARASOL (Polarization & Anisotropy of Reflectances for Atmospheric Sciences coupled with Observations from a Lidar) satellite's polarimeter made when a water cloud is present.

FIG. 7 shows the average results of PARASOL measurements made when a water cloud is present. The model assumes the data is taken over ocean and the solar zenith angle varies over a range of 25-30° in these measurements. The plot shows a very strong feature in the AOLP when 10°<VZA<45° and 120°<RAZ<180°, coinciding with the backscattering region. This anomaly appears like the number "8" and corresponds to a rotation of the AOLP to the p-polarization state. This is the glory feature due to the presence of the clouds. This negative polarization extends approximately 20° from the exact-backscattering direction, indicative of smaller water droplets than those used in the modeling of FIG. 7.

Figure 8:
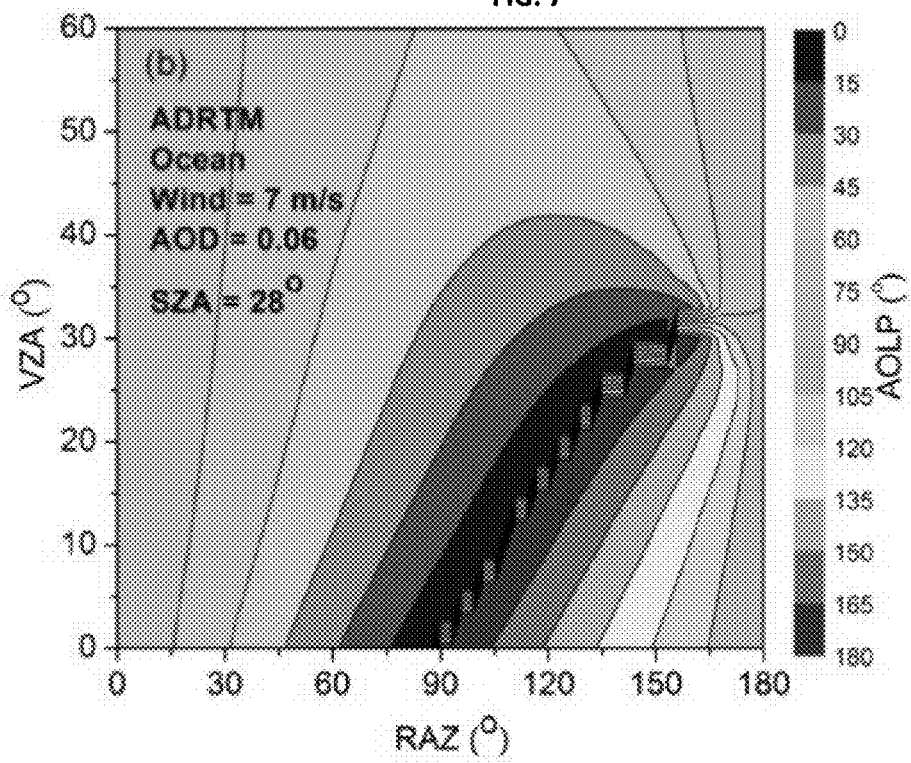
FIG. 8 shows results of the clear-sky AOLP calculated using the Adding Doubling Radiative-Transfer Model (ADRTM) that would be retrieved from the PARASOL polarimeter.

The plot of FIG. 8 shows results of the clear-sky AOLP calculated using the Adding Doubling Radiative-Transfer Model (ADRTM) that would be retrieved from the PARASOL polarimeter. The model assumes the data is taken over ocean with a wind speed of 7 m/s, and a solar zenith angle of 28°.

The AOLP calculation can be analyzed to identify clouds, super-thin clouds, or other phenomena. The angle of linear polarization of scattered sunlight observed in two distinct angular regions near the exact-backscatter direction rotates from an angle parallel to the Earth's surface to an angle that is perpendicular to the Earth's surface when cloud particles are present in the atmosphere. As shown in FIGS. 7 and 8, for a viewing zenith angle (VZA) smaller than the solar zenith angle (SZA), the AOLP at Relative Azimuth Angle (RAZ) of ~175-180° is of interest. If AOLP≤60°, then super-thin clouds exist. If 60°<AOLP<120°, then it is clear sky. If AOLP≥120°, then clouds or heavy aerosols are detected.

A sensitivity study demonstrates that cloud optical depth is necessary to see the polarization feature of the glory for cloud particles. This feature is detectable in water clouds having an optical depth of only about 0.01 and in ice clouds having an optical depth of only about 0.06, when the solar zenith angle (SZA) is not much larger than about 40° over a strong polarization background such as oceans. When over weak polarization background, the optical depth may be even smaller. Since most super-thin clouds are over the tropical and mid-latitude regions, this limit of SZA will not affect the detection of most super-thin clouds using the polarization features. Coupling this method with the total radiance measurements at a wavelength of about 1.38 μm would enhance the detection of super-thin clouds and thus can significantly improve retrieval of aerosol, water vapor or other gases, and surface temperature from satellite data. (The 1.38 μm wavelength is the location of a water-absorption band that may enhance the signal. It has been used in other applications, so it is likely that it may increase sensitivity).

The various measurements and/or calculations might be combined in some embodiments for more effective analysis.

The image processing from the instrumentation and analysis may be implemented as hardware, software or a combination thereof. For instance, it may be implemented with a computer or computing device having one or more processors (or micro-processors) as known in the art that are specifically configured to execute coding necessary to implement embodiments of the present invention. A designated image processor may be provided in some embodiments. Processor-executable instructions can be stored in a memory device and executed by the processors when needed. In some implementations, software code (instructions), firmware, or the like, may be stored on a computer or machine-readable storage media having computer or machine-executable instructions executable by the processor(s). The processor(s) may be a programmable processor, such as, for example, a field-programmable gate array (FPGA) or an application-specific integrated circuit (ASIC) processor. The methodology disclosed herein may be implemented and executed by an application may be created using any number of programming routines. Of course, any number of hardware and/or software implementations, programming languages, and operating platforms may be used without departing from the spirit or scope of the invention. As such, the description or recitation of any specific hardware implementation, programming language, and operating platform herein is exemplary only and should not be viewed as limiting.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the present disclosure and its practical applications, to thereby enable others skilled in the art to best utilize the invention and various embodiments with various modifications as may be suited to the particular use contemplated.

While the foregoing is directed to embodiments of the present invention, other and further embodiments of the invention may be devised without departing from the basic scope thereof, and the scope thereof is determined by the claims that follow.

We claim:

1. A method for detecting clouds, the method comprising:
   receiving data from a sensor which is configured to measure the polarization of an optical glory associated with a cloud, wherein the sensor is co-aligned with the direction of incident sunlight and measures the polarization of scattered light in a direction substantially opposite to the direction of the incident sunlight during measurement; and
   identifying, from the received sensor data, a cloud based on the polarization of the detected optical glory.

2. The method of claim 1, wherein the sensor is configured to measure the polarization of the scattered light diverging over a range of up to about 20° from the exact backscattered light direction of the incident sunlight.

3. The method of claim 1, the sensor is configured to measure the polarization of the scattered light diverging over a range of about 5-10° from the exact backscattered light direction of the incident sunlight.

4. The method of claim 1, wherein the sensor is configured to detect the s-polarization and p-polarization intensities of the measured scattered light.

5. The method of claim 4, wherein a cloud is identified if the detected p-polarization measurement is greater than the s-polarization measurement of the scattered light direction.

6. The method of claim 1, wherein the sensor or an image processor associated therewith is configured to provide the Stokes Parameters Q, U and I of polarization.

7. The method of claim 6, further comprising: calculating the degree of polarization normalized Mueller matrix element P12/P11 from the Stokes Parameters of polarization as follows:

$$P12/P11 = (I_S - I_P)/(I_S + I_P),$$

where $I_S$ is the intensity of the s-polarized component of the light and $I_P$ is the intensity of the p-polarized component of the light.

8. The method of claim 7, wherein a cloud is identified if the calculated P12/P11 is negative near the backscattered light direction.

9. The method of claim 6, further comprising: calculating the angle of linear polarization (AOLP) from Stokes Parameters of polarization as follows:

$$AOLP = \frac{1}{2}\tan^{-1}\left(\frac{U}{Q}\right) + \alpha_0,$$

where $\alpha_0 = 0°$ if Q>0 and U≥0; $\alpha_0 = 180°$ if Q>0 and U<0; and $\alpha_0 = 90°$ if Q≤0.

10. The method of claim 9, wherein a cloud is identified if the calculated AOLP≤about 60° or ≥120°.

11. The method of claim 1, wherein the sensor is located on a satellite orbiting the Earth.

12. The method of claim 11, further comprising: transmitting the sensor data from the satellite to a ground station, receiving the transmitted sensor data at the ground station, or both transmitting the sensor data to and receiving the sensor data from the ground station.

13. The method of claim 1, wherein only scattered sunlight is measured by the sensor.

14. The method of claim 1, further comprising: identifying, from the received sensor data, a super-thin cloud based on the polarization of the scattered sunlight.

15. A method for detecting cloud particles, the method comprising;
  receiving data from a sensor which is configured to measure the polarization of an optical glory associated with a cloud, wherein the sensor measures the polarization of the scattered light diverging from the exact backscattered light direction of incident sunlight to detect the optical glory; and
  identifying, from the received sensor data, cloud particles based on the polarization of the detected optical glory.

16. A system for detecting clouds, the system comprising:
  a sensor configured to measure the polarization of an optical glory associated with a cloud, wherein the sensor is configured to be co-aligned with the direction of incident sunlight and to measure the polarization of scattered light in a direction substantially opposite to the direction of the incident sunlight during measurement; and
  a processor configured to identify, from the measured sensor data, a cloud based on the polarization of the detected optical glory.

17. The system of claim 16, wherein the sensor comprises: at least one polarizer which filters incoming light having p-polarization, a lens which focuses the filtered light, and an image detector which receives the focused light.

18. The system of claim 17, wherein the at least one polarizer comprises (i) a rotating polarizer or (ii) three polarizers which are offset in angular orientation.

19. The system of claim 16, wherein the sensor is configured to measure the polarization of light having a wavelength of about 1.38 μm.

20. The system of claim 16, wherein the sensor is configured to measure the polarization of light having a wavelength of about 670 nm.

* * * * *